(12) United States Patent
Ota

(10) Patent No.: US 11,234,920 B2
(45) Date of Patent: Feb. 1, 2022

(54) MANUFACTURING METHOD OF AN ASCORBIC ACID DISPERSION MATERIAL

(71) Applicant: Takanori Ota, Musashino (JP)

(72) Inventor: Takanori Ota, Musashino (JP)

(*) Notice: Subject to any disclaimer, the term of this patent is extended or adjusted under 35 U.S.C. 154(b) by 199 days.

(21) Appl. No.: 16/587,765

(22) Filed: Sep. 30, 2019

(65) Prior Publication Data

US 2020/0030218 A1    Jan. 30, 2020

Related U.S. Application Data

(62) Division of application No. 15/557,682, filed as application No. PCT/JP2016/059343 on Mar. 24, 2016, now abandoned.

(30) Foreign Application Priority Data

Mar. 31, 2015    (JP) .................. 2015-074620

(51) Int. Cl.

| | |
|---|---|
| *A61K 8/67* | (2006.01) |
| *A61Q 19/08* | (2006.01) |
| *A61K 8/04* | (2006.01) |
| *A61Q 19/00* | (2006.01) |
| *A61K 47/10* | (2017.01) |
| *A61K 31/375* | (2006.01) |
| *A61K 8/34* | (2006.01) |

(52) U.S. Cl.
CPC .............. *A61K 8/676* (2013.01); *A61K 8/04* (2013.01); *A61K 8/345* (2013.01); *A61K 31/375* (2013.01); *A61K 47/10* (2013.01); *A61Q 19/00* (2013.01); *A61Q 19/08* (2013.01); *A61K 2800/412* (2013.01)

(58) Field of Classification Search
CPC .......... A61K 8/676; A61K 8/04; A61K 8/345; A61K 31/375; A61K 47/10; A61K 2800/412; A61Q 19/00; A61Q 19/08
See application file for complete search history.

(56) References Cited

U.S. PATENT DOCUMENTS

| | | | |
|---|---|---|---|
| 6,294,179 B1 * | 9/2001 | Lee .......................... | A61K 8/19 424/401 |
| 8,211,472 B2 * | 7/2012 | Okumura ............... | A61K 8/345 424/489 |

* cited by examiner

*Primary Examiner* — Genevieve S Alley
(74) *Attorney, Agent, or Firm* — Manabu Kanesaka

(57) ABSTRACT

A manufacturing method of an ascorbic acid dispersion material includes a heating step of adding an ascorbic acid into a solvent including one or more selected from the group consisting of glycerin, diglycerin, polyglycerin represented by a following formula, and propylene glycol, and heating the ascorbic acid to a predetermined temperature to dissolve the ascorbic acid; a cooling step of cooling a solution with the ascorbic acid dissolved therein at a cooling rate of 5 to 20° C./min until a temperature of the solution reaches 35 to 50° C. to remove heat from the solution; and a growth step of storing the solution after completion of the cooling step at 27 to 38° C. for a predetermined period to promote crystal growth so that the ascorbic acid crystal has a flat plate shape, a thickness of 0.05 to 3 μm, and an average particle diameter of 50 to 100 μm.

Chemical formula

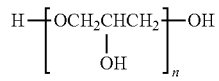

5 Claims, 8 Drawing Sheets

Appearance of particles (powder) extracted from sample GAG38

Appearance of particles (powder) extracted from sample GAG30

Appearance of particles (powder) extracted from sample GAG22

MANUFACTURING METHOD OF AN ASCORBIC ACID DISPERSION MATERIAL

CROSS-REFERENCE TO RELATED APPLICATION

This is a divisional Application of Ser. No. 15/557,682 filed on Sep. 12, 2017.

TECHNICAL FIELD

The present invention relates to an ascorbic acid dispersion material, as well as its manufacturing method.

BACKGROUND ART

Because ascorbic acid has an antioxidative action, and is involved in the generation and maintenance of collagen, thereby having an anti-aging effect on skin, ascorbic acid is blended into whitening cosmetics, etc., as a safe whitening material, and also as a whitening component for preventing spots and freckles, etc.

Moreover, ascorbic acid is also used in drugs for the prevention and treatment of vitamin C deficiency diseases, as well as for replenishment purposes, etc., and many other pharmacological effects are known. Examples of these pharmacological effects may include such effects as: (action on capillary blood vessels) reinforcement of capillary resistance, amelioration of bleeding tendencies, or increase in blood clotting; (action on adrenocortical functions) biosynthesis promotion or catabolism suppression with respect to steroid hormones, (action on connective tissues) involvement in the hydroxylation process from proline to hydroxyproline, and particularly in the case of collagen, in the formation/maintenance of an intercellular matrix and collagen, and in increasing collagen through the administration of ascorbic acid, (action on bone tissue) promoting bone formation, and (action on the generation of melanin pigment) inhibition of the oxidation process from dopa to dopaquinone during the process of generating melanin from tyrosine, and suppression of melanin pigment generation. As a result, ascorbic acid is also used for: treatment of capillary bleeding, such as nasal bleeding, gingival bleeding, and hematuria; dysadrenocorticism; bone matrix formation/bone union promotion in fractures; suppression of pigment deposition after chloasma/ephelides/inflammation; and chemical poisoning involving alcohol, nicotine, etc.

Further, ascorbic acid is also blended in with cold drinks, storage foods, confectionery, health foods, etc.

Unfortunately, when ascorbic acid is dissolved in water, it becomes very unstable, and easily oxidized as a result of light, heat, the pH state, metal ions, etc.; even if a highly concentrated aqueous solution of ascorbic acid is prepared, it is difficult to store in a stable manner. Moreover, while ascorbic acid is useful as a percutaneous absorption-type pharmaceutical such as cosmetic materials, as mentioned above, the high concentration is problematic in that it enables crystallization, leading to poor usage characteristics.

For this reason, various technologies have been proposed relating to ascorbic acid dispersion liquids, etc., that are able to stably store ascorbic acid at a high concentration, as well as various dispersion liquids in which even at high concentrations usage characteristics do not worsen.

For example, a percutaneous absorption liquid including an ascorbic acid suspension liquid containing ascorbic acid particles of less than 20 μm, etc., is proposed.

Moreover, the present applicants have so far proposed, in Patent Documents 1 and 2, for example, a glycerin liquid suspension of an ascorbic acid that is useful as a cosmetic substrate containing ascorbic acid having superior usage characteristics (spreadability and smoothness upon application onto skin), wherein the content of the ascorbic acid is 13% by mass or more, and part of the ascorbic acid is dissolved in glycerin or glycerin-containing diglycerin, at a concentration of 8 to 12% by mass, while the remaining ascorbic acid is deposited as a fine crystal having a particle diameter of 25 μm or smaller, and homogeneously dispersed.

Moreover, for example, Patent Document 3 proposes, as a manufacturing method for a homogeneous solution of transparent and stable glycerin containing a high concentration of ascorbic acid, as well as a cosmetic material including the glycerin solution, a manufacturing method for a glycerin solution having an ascorbic acid concentration of 16 to 45% by mass, wherein an ascorbic acid, glycerin, and ethyl alcohol are mixed to dissolve the ascorbic acid, and subsequently the ethyl alcohol is removed, as well as a cosmetic material including the glycerin solution.

Moreover, for example, Patent Document 4 proposes, as a stable storage method providing superior quality in a glycerin solution containing a high concentration of ascorbic acid, a low temperature storage method that stores a glycerin solution having an ascorbic acid concentration of 13% by mass or higher, at 0° C. to −30° C.

PRIOR ART DOCUMENTS

Patent Documents

Patent Document 1: International Publication WO No. 2008/050676
Patent Document 2: Japanese Unexamined Patent Application Publication No. 2013-166778
Patent Document 3: Japanese Unexamined Patent Application Publication No. 2007-332094
Patent Document 4: Japanese Unexamined Patent Application Publication No. 2008-013493

SUMMARY OF THE INVENTION

Problems to be Solved by the Invention

Unfortunately, percutaneous absorption liquids, including the ascorbic acid suspension liquid containing ascorbic acid particles of less than 20 μm as mentioned above, etc., have crystal particles that are too small, poor storage stability, and poor usage characteristics and absorption as a percutaneous absorption type pharmaceutical.

Moreover, in the proposals in Patent Documents 1 to 4, while there is improved chemical stability of ascorbic acid, as well as spreadability and smoothness upon application onto skin, even more advanced usage characteristics and storage stability are currently required.

For this reason, there is a demand for the development of ascorbic acid dispersion materials that have higher chemical stability and superior usage characteristics, such as spreadability and smoothness upon application onto skin.

Accordingly, the object of the present invention is to provide an ascorbic acid dispersion material that has higher chemical stability, and superior usage characteristics, such as spreadability and smoothness upon application onto skin.

Means for Solving the Problems

As a result of extensive research in order to solve the abovementioned problems, the present inventors found that the crystalline form of ascorbic acid varies under conditions of heating, cooling, and crystal growth in the manufacturing method of an ascorbic acid dispersion material, and it was also found that there are a suitable particle diameter range and particle shape that improve usage characteristics according to the particle diameter of the crystal particles, leading to the completion of the present invention.

In other words, the present invention provides each of the following inventions.

1. An ascorbic acid dispersion material, which is obtained by dispersing an ascorbic acid crystal in a solvent, wherein the ascorbic acid crystal has a flat plate shape, and an average particle diameter of 50 to 100 μm.
2. The ascorbic acid dispersion material according to 1, wherein the particle size distribution of the ascorbic acid crystal has a distribution such that particles having a particle diameter of 30 to 120 μm account for 40 to 80% of the overall particles.
3. The ascorbic acid dispersion material according to 1, wherein the solvent contains glycerin.
4. The ascorbic acid dispersion material according to 1, wherein the ascorbic acid concentration is 20 to 40 wt %.
5. The ascorbic acid dispersion material described, wherein the ascorbic acid crystal has a thickness of 0.05 to 3 μm.
6. The ascorbic acid dispersion material according to 1, wherein the average density is 1.3 to 1.4 g/cm$^3$.
7. The ascorbic acid dispersion material according to 1, wherein the viscosity is 5000 to 300,000 mPa·s.
8. A manufacturing method of an ascorbic acid dispersion material according to 1, including: a heating step involving infusing an ascorbic acid into a solvent, and heating the ascorbic acid to a predetermined temperature to dissolve the ascorbic acid; a cooling step involving cooling the solution with the ascorbic acid dissolved therein to remove heat from the solution; and a growth step involving storing the solution after completion of the cooling step for a predetermined period to promote crystal growth.

Effects of the Invention

The ascorbic acid dispersion material of the present invention has higher chemical stability, and superior usage characteristics, such as spreadability and smoothness upon application onto skin.

Moreover, the manufacturing method of the present invention enables the ascorbic acid dispersion material of the present invention to be more efficiently manufactured.

MODE FOR CARRYING OUT THE INVENTION

While not limited to the following, the ascorbic acid dispersion material of the present invention will now be described.

(Overall Configuration of the Ascorbic Acid Dispersion Material)

The ascorbic acid dispersion material of the present invention is obtained by dispersing an ascorbic acid crystal in a solvent, wherein the abovementioned ascorbic acid crystal has a specific shape and particle diameter.

The shape and particle diameter of the abovementioned ascorbic acid crystal will be described in detail later.

(Solvent)

While the abovementioned solvent used in the present invention is not particularly limited, for example, glycerin, diglycerin, polyglycerin represented by the following formula, propylene glycol, etc., can be used, and any one of these may be used, or two or more of these may be mixed and used.

[Chemical formula 1]

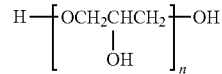

In the formula, n is an integer from 3 to 10.

Among other possibilities, the solvent is preferably glycerin and diglycerin, from the perspective that ascorbic acid tends to have the crystal shape described below, and from the perspectives of safety to the human body including skin, and usage characteristics upon application onto skin. Moreover, in obtaining a mixed solvent of glycerin and diglycerin, the blending ratio of diglycerin is preferably 0.1 to 5 wt % in the solvent.

(Ascorbic Acid Crystal)

Figure 2:
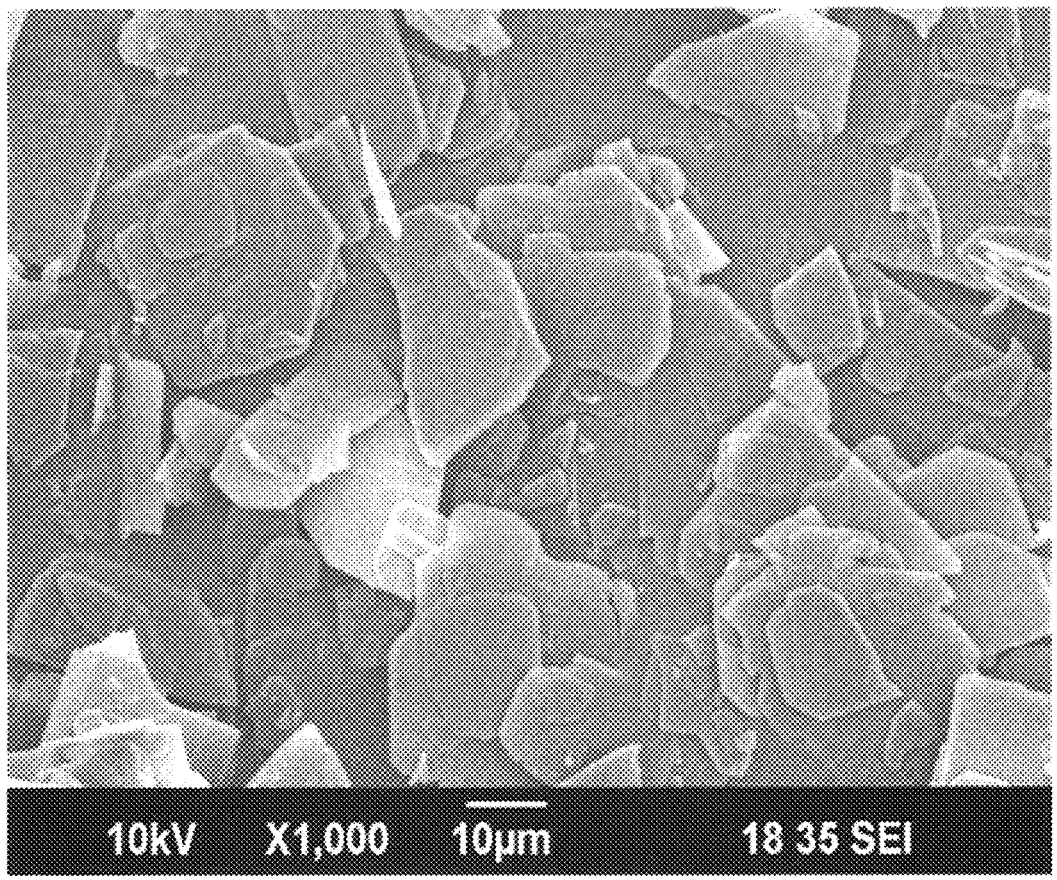
FIG. 2 is a scanning electron micrograph image (drawing substitute photograph) of an ascorbic acid crystal in Example 2.
Figure 3:
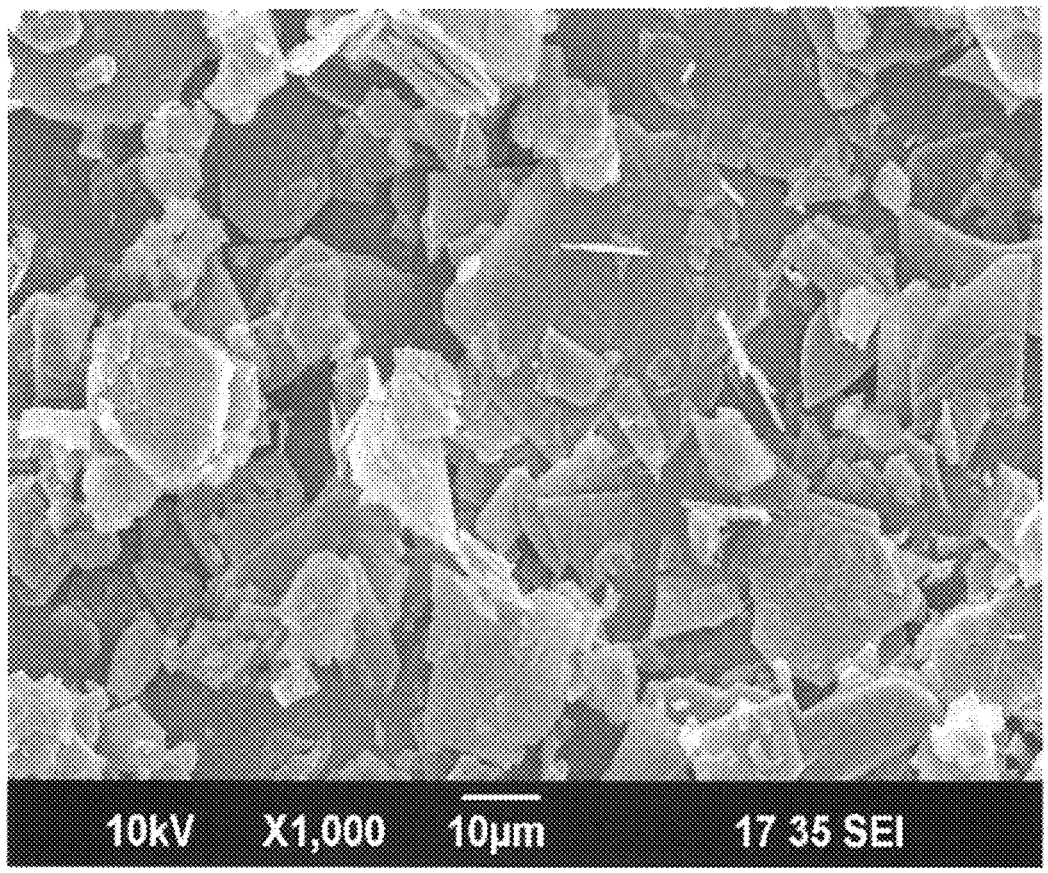
FIG. 3 is a scanning electron micrograph image (drawing substitute photograph) of an ascorbic acid crystal in Example 3.

The abovementioned ascorbic acid crystal in the ascorbic acid dispersion material of the present invention has a flat plate shape. Moreover, the abovementioned ascorbic acid crystal has gentle angles in the corners, with few sharp angles (see FIGS. 1 to 3)

As a result, the ascorbic acid dispersion material of the present invention has a smoothness upon application onto skin, with superior usage characteristics. Moreover, it is not known why the crystals tend to not be aggregated, as a result of which the chemical stability of the ascorbic acid is increased.

Note that while crystals having shapes other than a flat plate shape, such as a sphere, may be present among the ascorbic acid crystals, the ratio of such crystals is generally 10 wt % or lower.

While the thickness of the abovementioned ascorbic acid crystal is not particularly limited, it is preferably 0.05 to 3 µm. Within this range, the abovementioned usage characteristics are superior.

Note that the thickness of the abovementioned ascorbic acid crystal used herein is obtained by randomly selecting 100 crystals from a scanning electron microscope image, obtaining the thickness of each of the selected crystals by image analysis, and obtaining the average value thereof. Moreover, the particle shape, etc. is obtained using a scanning electron microscope, and measured using the particulate powder obtained in the measurement of the particle diameter described below.

(Particle Diameter)

The average particle diameter of the abovementioned ascorbic acid crystal is 50 to 100 µm, preferably 60 to 95 µm. Within this range, the abovementioned usage characteristics are superior.

Note that the abovementioned average particle diameter and shape of particles are measured using the following method.

Method:
1. Commercially available ascorbic acid crystals are infused into acetone, and dissolved to obtain a saturated state.
2. Fine particulate crystals of the ascorbic acid present in the ascorbic acid saturated acetone solution of 1 are subjected to ultracentrifugation using a generally known ultracentrifuge via a generally known method, to precipitate and remove particles of the ascorbic acid, thus preparing an ascorbic acid saturated acetone solution (hereinafter, referred to as a dispersion medium) not containing fine particulate crystals of the ascorbic acid.
3. A small amount (5 mL) of the ascorbic acid dispersion material of the present invention, as an analyte, is infused into 20 mL of the dispersion medium prepared in 2, lightly shaken, and mixed.
4. The suspension liquid of 3 is subjected to ultracentrifugation using an ultracentrifuge under generally known conditions, to precipitate particles of the ascorbic acid, and remove the supernatant.
5. 20 mL of the dispersion medium prepared in 2 is added to the obtained precipitate, lightly shaken, and dispersed.
6. The operations of 4 and 5 are further carried out to remove the solvent component of the ascorbic acid dispersion material of the present invention, following which the operation of 4 is further carried out to precipitate particles of the ascorbic acid, and remove the supernatant, and the particles are then dried at a low temperature to obtain particulate powder.
7. An appropriate amount of hexane for measuring the particle size distribution is added to the particulate powder obtained in 6, to slightly disperse the precipitate, and obtain a sample for particle size analysis.
8. The sample of 7 for particle size analysis is subjected to measurement of its laser diffraction/scattering particle diameter distribution.

Note that it was found (not illustrated) that the particle diameter and particle shape that are measured after grinding commercially available ascorbic acid crystals and dispersing them in hexane are not significantly different from the particle diameter and particle shape which are measured using the abovementioned method after grinding commercially available ascorbic acid crystals. As a result, the particles extracted via the abovementioned method are able to faithfully reproduce the shape and particle diameter of the particles in the dispersion material.

(Particle Size Distribution)

While the particle size distribution of the abovementioned ascorbic acid crystal is not particularly limited, particles having a particle diameter of 30 to 120 µm account for preferably 40 to 80%, more preferably 50 to 75%, of the overall particles. Within this range, the abovementioned usage characteristics are superior.

Note that the abovementioned particle size distribution refers to the value that is obtained by a laser diffraction/scattering particle diameter distribution measurement using the sample for particle size analysis obtained in the abovementioned particle diameter measurement method.

(Ascorbic Acid Concentration)

While the concentration of the ascorbic acid in the ascorbic acid dispersion material of the present invention is not particularly limited, the ascorbic acid in the overall ascorbic acid dispersion material is preferably 10 to 45 wt %, and more preferably 20 to 40 wt %. Within this range, the ascorbic acid can be effectively used at a high concentration; and in case where it is used for cosmetics, skin care preparations, etc., the effects on skin are superior.

Note that while the state of the ascorbic acid in the abovementioned concentration is not particularly limited, examples thereof may include crystal and noncrystal states, as well as the state of being dissolved in a solvent, etc.

(Density)

While the density of the ascorbic acid dispersion material of the present invention is not particularly limited, the average density is preferably 1.30 to 1.40 g/cm$^3$, and more preferably 1.31 to 1.39 g/cm$^3$. Within this range, the ascorbic acid can be effectively used at a high concentration; and in cases where it is used for cosmetics, skin care preparations, etc., the abovementioned effects and usage characteristics are superior.

Note that the abovementioned density refers to a value measured using a dry densimeter.

(Viscosity)

While the viscosity of the ascorbic acid dispersion material of the present invention is not particularly limited, the average viscosity is preferably 5000 to 300000 mPa·s, and more preferably 8000 to 240000 mPa·s, from the perspectives of storage stability and usage characteristics. Within this range, the ascorbic acid can be effectively used at a high concentration; and in cases where it is used for cosmetics and skin care preparations, etc., the abovementioned usage characteristics are superior.

The abovementioned average viscosity used herein refers to a value measured using a Brookfield rotation viscometer under temperature conditions of 20° C.

(Manufacturing Method)

While the manufacturing method for the ascorbic acid dispersion material of the present invention is not particularly limited, it is preferably manufactured via the manufacturing method of the present invention, described below.

The manufacturing method of the present invention includes: a heating step involving infusing an ascorbic acid into a solvent, and heating the ascorbic acid to a predetermined temperature to dissolve the ascorbic acid; a cooling step involving cooling the solution with the ascorbic acid dissolved therein to remove the heat of the solution; and a growth step involving storing the solution after the completion of the abovementioned cooling step for a predetermined period to promote crystal growth.

As a result, the ascorbic acid dispersion material of the present invention can be more efficiently manufactured.

Below, each step will be described.

[Heating Step]

The abovementioned heating step refers to a step involving infusing an ascorbic acid into a solvent, and heating the ascorbic acid to a predetermined temperature to dissolve the ascorbic acid.

While the raw material of the abovementioned ascorbic acid is not particularly limited, for example, crystal powder of a commercially available ascorbic acid, etc. can be used, and may be subjected to treatment such as grinding, etc.

The abovementioned solvent is as mentioned above, and for example, glycerin, etc., can be used.

While the method for infusing an ascorbic acid into the abovementioned solvent is not particularly limited, it can be carried out via methods such as a method for directly infusing the raw material powder of the abovementioned ascorbic acid into the abovementioned solvent.

After infusing the raw material powder of the ascorbic acid into the abovementioned solvent, and subsequently heating it to a predetermined temperature, the raw material powder of the ascorbic acid is dissolved.

While the temperature of the abovementioned heating varies based on the shape/concentration of the ascorbic acid of the raw material, the kind of solvent, etc., the temperature of the solvent is preferably 100 to 125° C.

Moreover, the method of the abovementioned dissolution is preferably carried out by stirring, from the perspectives of the dissolution speed and homogeneous dispersion. Note that stirring under the abovementioned heating temperature conditions can be carried out via known methods. For example, it can be carried out by heating using known heating devices, and using known stirring machines.

Moreover, while heating in the abovementioned dissolution varies based on the shape/concentration of the ascorbic acid of the raw material, the kind of solvent, etc., this heating is preferably rapidly finished after the completion of the dissolution, from the perspectives of preventing the modification and decomposition of the ascorbic acid due to excessive heating.

For example, in cases where the abovementioned solvent is glycerin, the completion of the abovementioned dissolution is determined when the color of the mixed liquid changes, becoming transparent.

Moreover, the container for carrying out the abovementioned dissolution is not particularly limited as long as the container is tolerant to the solvent, the ascorbic acid, etc., and also tolerant to the temperatures in this heating step and the cooling step described below; for example, containers made of glass or plastic can be used. While the shape of the abovementioned container is also not particularly limited, general beakers and flask shapes can be used. Moreover, the abovementioned container is preferably a container having sealing and shading properties because storage after manufacturing the ascorbic acid dispersion liquid of the present invention can be carried out in the same container.

Note that, as required, the abovementioned dissolution can be carried out in an inert gas stream such as a nitrogen gas.

[Cooling Step]

The abovementioned cooling step refers to a step involving cooling the solution with the ascorbic acid dissolved therein, as obtained after the abovementioned heating step, to remove heat from the solution.

While the method of the abovementioned cooling is not particularly limited, the cooling speed is preferably 5 to 20° C./min. Such cooling can be carried out by a method involving, after the completion of the abovementioned heating step, immersing the container used in the abovementioned heating step into water with the solution contained in the container. While water used in this case is not particularly limited, tap water can be used as is. Moreover, a sufficient amount of water is preferably used for cooling to the temperatures described below, with the temperature generally being preferably approximately 4 to 20° C.

The removal of heat in this step is intended to set the temperature in the internal solution to 35 to 50° C., preferably approximately 40° C.; once it reaches a temperature within this range, the removal of heat is completed.

[Growth Step]

The abovementioned growth step refers to a step involving storing the solution after the abovementioned cooling step for a predetermined period to promote crystal growth.

The abovementioned growth step can be carried out by keeping the abovementioned solution after the abovementioned cooling step at preferably 27 to 38° C., more preferably approximately 30° C.

The abovementioned growth step is carried out for a period of 5 hours or longer, until the abovementioned crystal grows to be the desired size (particle diameter, thickness).

While the abovementioned specific period varies depending on the kind of solvent, the concentration of the ascorbic acid, etc., for example, in cases where the abovementioned solvent is glycerin, and the ascorbic acid is 10 to 45 parts by weight in 100 parts by weight of the total amount of the ascorbic acid and glycerin, the abovementioned period is 3 hours or longer, and preferably half a day or longer.

After carrying out the abovementioned growth step, the ascorbic acid dispersion material of the present invention can be obtained.

When the ascorbic acid dispersion material of the present invention is manufactured as mentioned above, it is possible to obtain the abovementioned ascorbic acid crystals in the dispersion material of the present invention, which are not conventionally obtained.

For example, there is a method involving heating to dissolve, then quenching using dry ice, thereby rapidly generating a large number of crystal cores. Because a large number of crystal cores develop, the number of molecules available for crystal growth decreases, and the cores grow to be crystal particles having a small crystal particle diameter. Moreover, rapid cooling also allows the viscosity of glycerin, which is a solvent, to rapidly increase giving rise to a small value for the degrees of freedom in the solution. For this reason, crystal growth tends to not occur, and this presumably gives rise to crystals having a small particle diameter (crystals having a smaller particle diameter than the abovementioned ascorbic acid crystal).

In contrast, in the present invention, heat is simply removed instead of cooling, and therefore crystal cores gradually develop. For this reason, crystal growth can be sufficiently promoted, and well-formed crystals can be obtained. Moreover, because the growth step can be carried out with a high value for the degrees of freedom in glycerin, this also allows the growth of crystal to be sufficiently carried out, and allows a dispersion material, in which ascorbic acid crystals having the abovementioned characteristic crystal shape is dispersed, to be obtained.

Below, applications and usage methods for the ascorbic acid dispersion material of the present invention are described.

(Applications)

Because the dispersion material of the ascorbic acid according to the present invention has the abovementioned properties, it can be used in various applications such in cosmetics, skin care preparations, quasi drugs, drugs, storage liquids for ascorbic acid, and food additives. Among others, because the ascorbic acid has effects such as antioxidative action, the generation and maintenance of collagen, and skin whitening, it can be suitably used in cosmetics and skin care preparations.

(Usage Methods)

In cases where the ascorbic acid dispersion material of the present invention is used in cosmetics and skin care preparations, the ascorbic acid dispersion material of the present invention can be used by application onto skin.

Note that in cases where the ascorbic acid dispersion material of the present invention is used in cosmetics and skin care preparations, the abovementioned solvent is preferably a solvent containing glycerin, from the perspective of safety to human body, including skin, as well as usage characteristics upon application onto skin (stimulation aspect), etc. Moreover, in cases where it is used in cosmetics and skin care preparations, the preferable aspect regarding crystals of the abovementioned ascorbic acid is as mentioned above.

(Storage)

Because redissolution starts when the ascorbic acid dispersion material of the present invention is 25° C. or higher, it is preferably stored at 25° C. or lower. Moreover, shaded storage is preferable from the perspective of preventing the decomposition caused by light. Moreover, nitrogen gas, etc. is preferably enclosed, substituted, etc., and followed by sealing and storing, in order to prevent the decomposition and modification of the ascorbic acid due to dissolved oxygen. Such storage enables the decomposition/modification of the ascorbic acid to be suppressed, allowing storage for further extended periods of time.

While the present invention is not limited to the abovementioned embodiments, various modifications can be made without departing from the spirit of the present invention.

For example, the ascorbic acid dispersion material of the present invention can contain other components without departing from the spirit of the present invention. Examples of such other components may include useful components used for formulations such as drugs, quasi drugs, and cosmetics, for example, ultraviolet inhibitors, whitening agents, perfumes, etc. Moreover, the abovementioned other components can be blended during the abovementioned heating step to cooling step, after the completion of the cooling step, etc., with the timing of such blending not being particularly limited.

Examples

While not limited thereto, the present invention will be described below in further detail using examples and comparative examples.

Example 1

(Manufacture of the Ascorbic Acid Dispersion Material)
[Heating Step]

38 g of an ascorbic acid raw material fine powder (pharmacopeia, produced by DSM Nutrition) and 62 g of glycerin as a solvent were each weighed, and infused into a conical flask made of glass. After infusing, the mixture was heated such that the temperature thereof reached 115° C., and stirred using a blade type stirring device Immediately after the temperature of the mixture reached 115° C., the color of the mixed liquid changed from yellow to transparent. As a result, the fact that the ascorbic acid was completely dissolved was confirmed, and the heating step was thus completed.

[Cooling Step]

The temperature in the conical flask after the completion of the abovementioned heating step was monitored with 5 L of tap water at a temperature of 20° C., using a temperature meter, and it was cooled until the temperature of the mixture reached 40° C.

Note that the cooling period was 5 minutes.

[Growth Step]

The conical flask after the completion of the abovementioned cooling step was sealed with a rubber plug, placed into an incubator having a temperature of 30° C., and left for 3 days to obtain the ascorbic acid dispersion material of the present invention (hereinafter, also referred to as GAG38) having an ascorbic acid concentration of 38 wt %.

Example 2

An ascorbic acid dispersion material of the present invention (hereinafter, also referred to as GAG30) having an ascorbic acid concentration of 30 wt % was obtained as in Example 1, except that 30 g of ascorbic acid raw material fine powder and 70 g of glycerin as a solvent were used in the heating step, and the temperature retention time in the growth step was 2 days.

Example 3

An ascorbic acid dispersion material of the present invention (hereinafter, also referred to as GAG22) having an ascorbic acid concentration of 22 wt % was obtained as in Example 1, except that 22 g of ascorbic acid raw material fine powder and 78 g of glycerin as a solvent were used in the heating step, and the temperature retention time in the growth step was 1 day.

Test Example 1 Observation of the Crystals Using a Scanning Electron Microscope

The ascorbic acid crystals contained in the ascorbic acid dispersion material of the present invention obtained in Examples 1 to 3 were observed using a scanning electron microscope.

Note that as a control sample, crystals of commercially available ascorbic acid were ground using a mortar, and observed alongside.

(Preparation of Samples for the Scanning Electron Microscope)

Samples for the scanning electron microscope were prepared via the following method.

Method:

1. Ascorbic acid crystals were infused into acetone, and dissolved to obtain a saturated state.

2. Fine particulate crystals of the ascorbic acid present in the ascorbic acid saturated acetone solution of 1 were subjected to ultracentrifugation using an ultracentrifuge under generally known conditions, to precipitate and remove particles of the ascorbic acid, thus preparing an ascorbic acid saturated acetone solution (hereinafter, referred to as the dispersion medium) not containing fine particulate crystals of the ascorbic acid.

3. 5 mL of the ascorbic acid dispersion material of the present invention obtained in Examples 1 to 3 as an analyte and 0.5 g of commercially available ascorbic acid powder were both infused into 20 mL of the dispersion medium prepared in 2, lightly shaken, and mixed.

4. The suspension liquid of 3 was subjected to ultracentrifugation using an ultracentrifuge under generally known conditions, to precipitate particles of the ascorbic acid, and remove the supernatant.

5. 20 mL of the dispersion medium prepared in 2 was added to the obtained precipitate, lightly shaken, and dispersed.

6. The operations of 4 and 5 were further carried out to remove the solvent component of the ascorbic acid dispersion material of the present invention, following which the operation of 4 was further carried out to precipitate particles of the ascorbic acid, and remove the supernatant, and the particles were dried at a low temperature to obtain particulate powder.

7. The obtained particulate powder was used as a sample for the scanning electron microscope.

(Observation Using a Scanning Electron Microscope)

Regarding the obtained sample for a scanning electron microscope, an electron microscope image was acquired using a scanning electron microscope under the following conditions, and the acquired image was observed.

Conditions:
acceleration voltage: 10 kV
magnification: 1000 times (5000 times for the ascorbic acid powder of the control sample)

Figure 1:
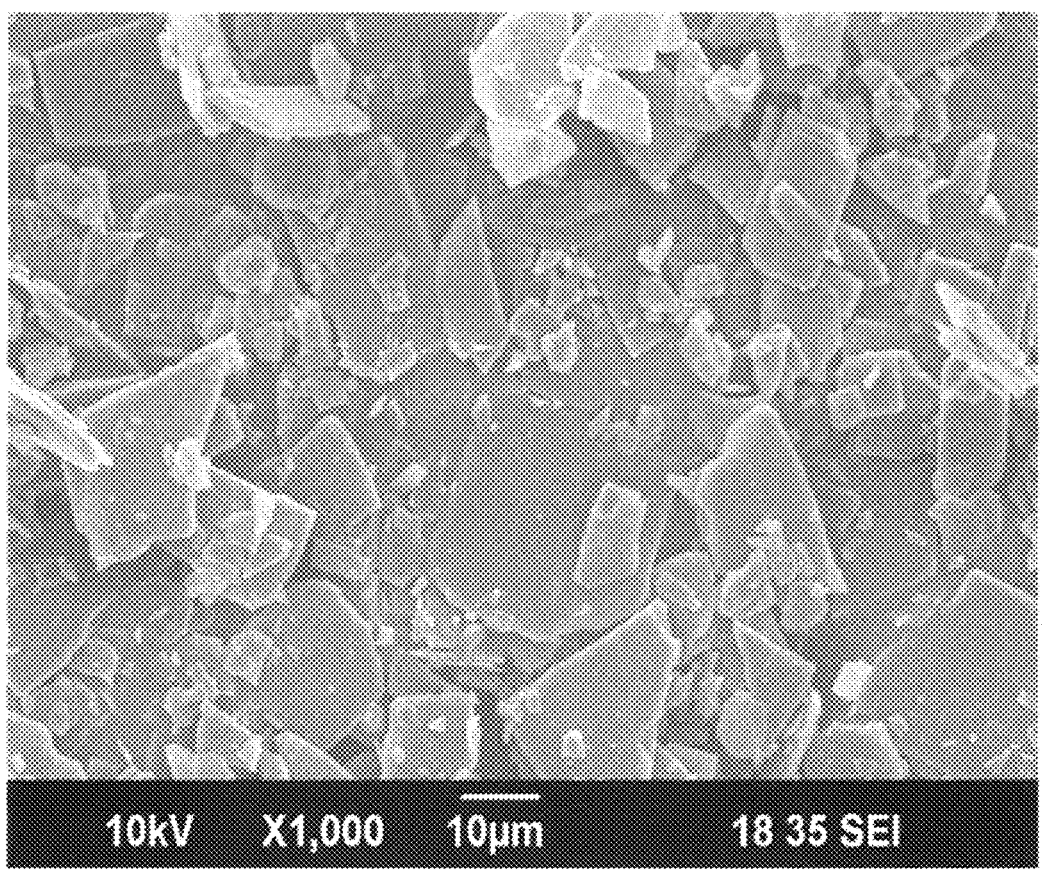
FIG. 1 is a scanning electron micrograph image (drawing substitute photograph) of an ascorbic acid crystal in Example 1.
Figure 4:
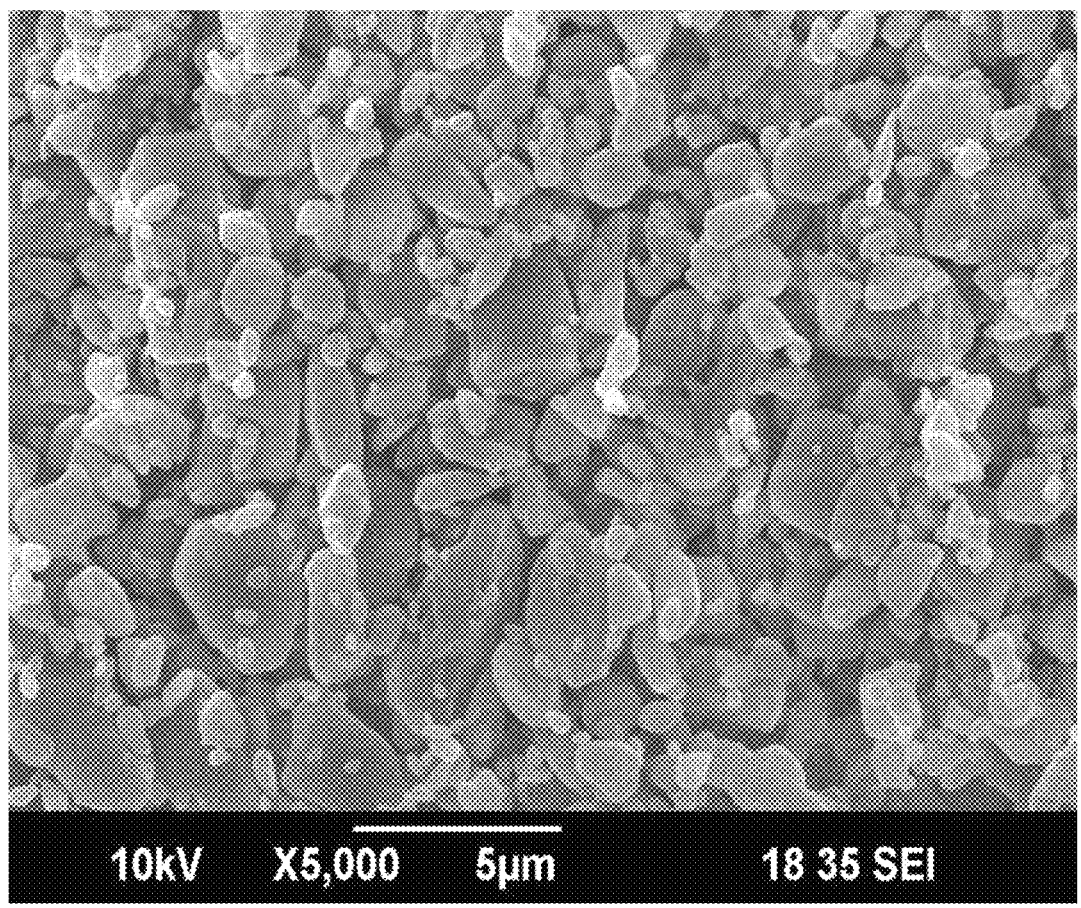
FIG. 4 is a scanning electron micrograph image (drawing substitute photograph) of a commercially available ascorbic acid crystal powder.

The obtained results are shown in FIG. 1 (Example 1: GAG38), FIG. 2 (Example 2: GAG30), FIG. 3 (Example 3: GAG22), and FIG. 4 (control testing: commercially available ascorbic acid crystal powder).

(Measurement of the Crystal Thickness)

Further, 100 crystals were randomly selected from the obtained scanning electron microscope image, and an image analysis of the obtained scanning electron microscope image was carried out to obtain the average value of the thickness of the selected crystals.

The results thereof are shown below.
Average value of the crystal thickness:
Example 1 (GAG38): 1.194 μm
Example 2 (GAG30): 1.040 μm
Example 3 (GAG22): 0.924 μm (Results and Remarks)

The results show that most of the ascorbic acid crystals contained in the ascorbic acid dispersion material of the present invention obtained in Examples 1 to 3 have a flat plate shape, have gentle angles at the corners with few sharp angles, and have a low thickness with small variations in thickness.

In contrast, the results show that the ascorbic acid crystal powder, which is an object sample, has an indeterminate crystal shape, which is totally different from the crystal shape of the ascorbic acid contained in the ascorbic acid dispersion material of the present invention.

Due to properties of the crystal structure, the ascorbic acid dispersion material of the present invention is presumed to have superior usage characteristics upon application onto skin.

Test Example 2 Particle Size Analysis

A particle size analysis of the ascorbic acid crystals contained in the ascorbic acid dispersion material of the present invention obtained in Examples 1 to 3 was carried out.

(Preparation of Samples for Particle Size Analysis)

Samples for particle size analysis were prepared from the ascorbic acid dispersion material of the present invention obtained in Examples 1 to 3, as in Steps 1 to 6 of the method used to obtain particulate powder in preparing samples for the scanning electron microscope of Test Example 1, an appropriate amount of hexane for measuring the particle size distribution was added to the particulate powder, and the precipitate was slightly dispersed to obtain samples for particle size analysis.

(Particle Size Analysis)

Figure 5:
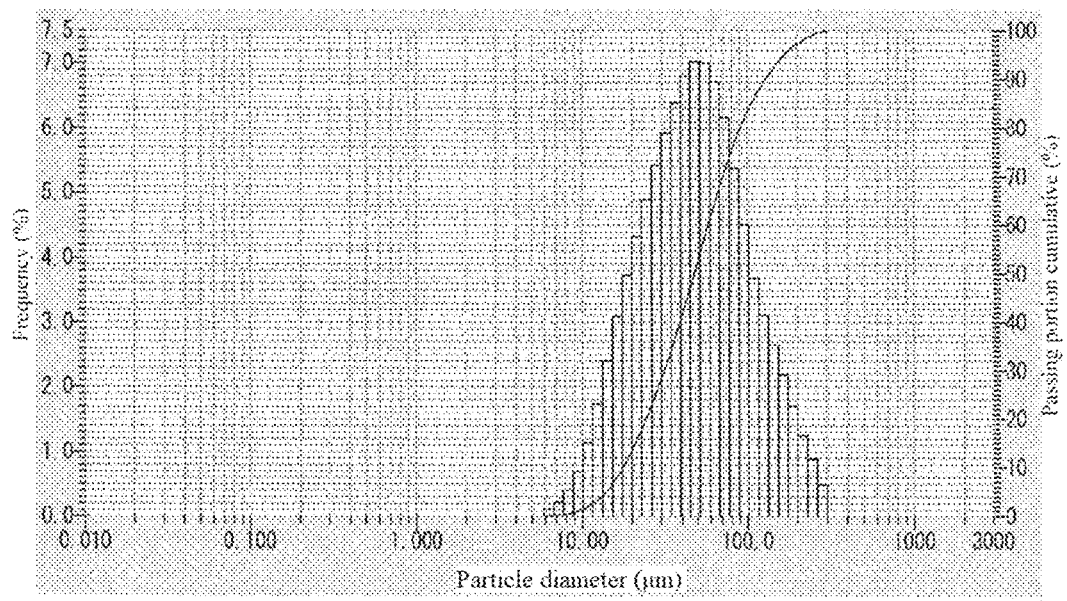
FIG. 5 is a chart illustrating the results of the particle size distribution analysis of an ascorbic acid dispersion material in Example 1.
Figure 6:
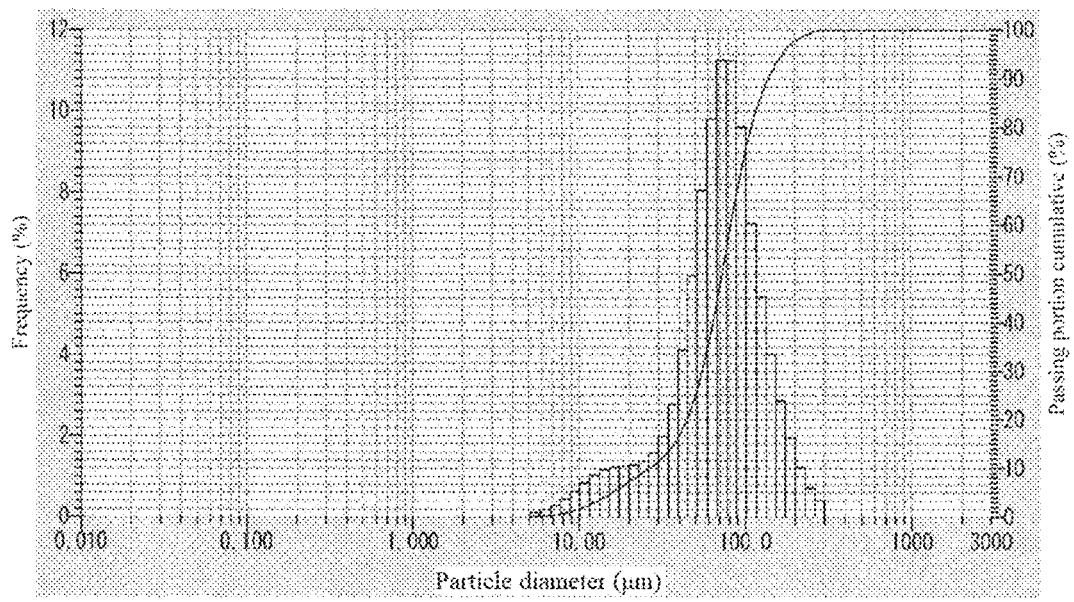
FIG. 6 is a chart illustrating the results of the particle size distribution analysis of an ascorbic acid dispersion material in Example 2.
Figure 7:
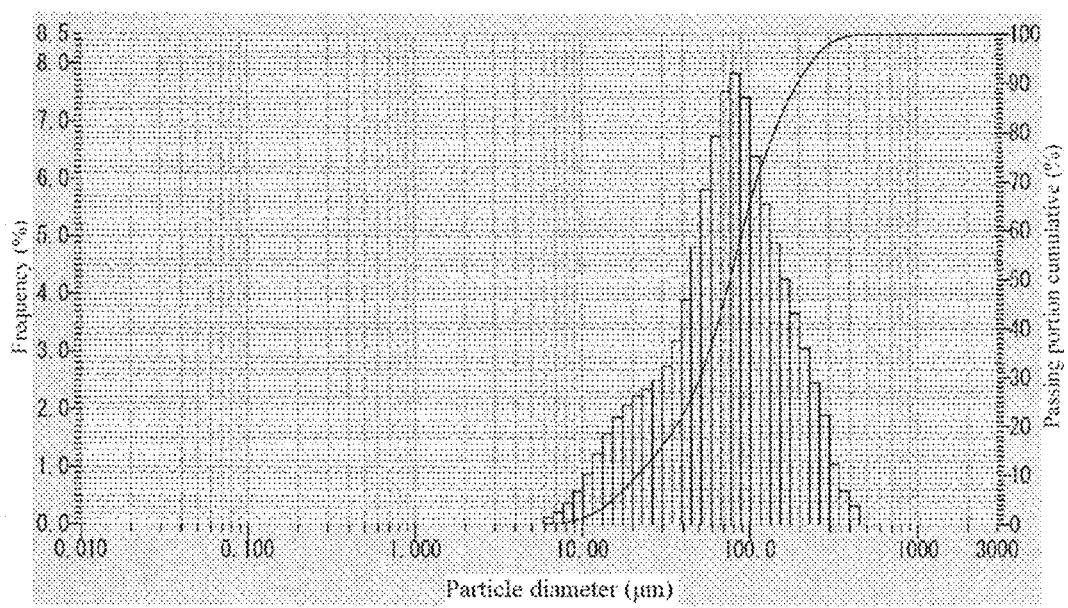
FIG. 7 is a chart illustrating the results of the particle size distribution analysis of an ascorbic acid dispersion material in Example 3.
Figure 8:
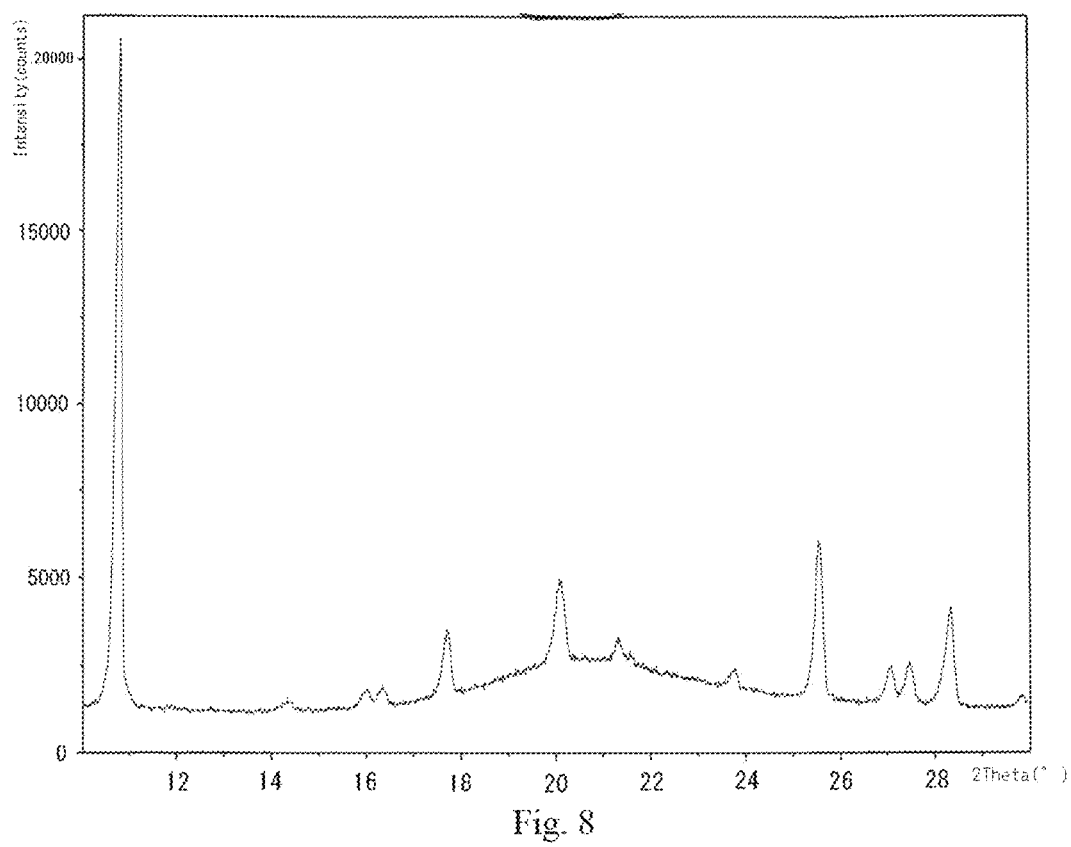
FIG. 8 is a chart illustrating the results of the X-ray diffraction analysis of the ascorbic acid crystal in Example 1.

The particle size analysis of the obtained samples for particle size analysis was carried out using a laser diffraction/scattering particle diameter distribution measurement device (type name: LA-950V2, manufactured by Horiba, Ltd.). The obtained results (histogram) are shown in FIG. 5 (Example 1: GAG38), FIG. 6 (Example 2: GAG30), and FIG. 7 (Example 3: GAG22).

The results (particle diameter and frequency) are shown in Table 1 (Example 1: GAG38), Table 2 (Example 2: GAG30), and Table 3 (Example 3: GAG22).

Moreover, the average particle diameter, the median diameter, the mode diameter, and the ratio of particles having a particle diameter of 30 to 120 μm are shown in Table 4.

TABLE 1

| No. | Particle diameter (μm) | Frequency (%) | Passing portion cumulative (%) |
|---|---|---|---|
| 35 | 1.151 | 0.000 | 0.000 |
| 36 | 1.318 | 0.000 | 0.000 |
| 37 | 1.510 | 0.000 | 0.000 |
| 38 | 1.729 | 0.000 | 0.000 |
| 39 | 1.981 | 0.000 | 0.000 |
| 40 | 2.269 | 0.000 | 0.000 |
| 41 | 2.599 | 0.000 | 0.000 |
| 42 | 2.976 | 0.000 | 0.000 |
| 43 | 3.409 | 0.000 | 0.000 |
| 44 | 3.905 | 0.000 | 0.000 |
| 45 | 4.472 | 0.000 | 0.000 |
| 46 | 5.122 | 0.000 | 0.000 |
| 47 | 5.867 | 0.000 | 0.000 |
| 48 | 6.720 | 0.108 | 0.108 |
| 49 | 7.097 | 0.215 | 0.324 |
| 50 | 8.816 | 0.397 | 0.721 |
| 51 | 10.097 | 0.687 | 1.407 |
| 52 | 11.565 | 1.138 | 2.546 |
| 53 | 13.246 | 1.728 | 4.274 |
| 54 | 15.172 | 2.402 | 6.076 |
| 55 | 17.377 | 3.085 | 9.761 |
| 56 | 19.904 | 3.729 | 13.490 |
| 57 | 22.797 | 4.328 | 17.818 |
| 58 | 26.111 | 4.892 | 22.709 |
| 59 | 29.907 | 5.424 | 28.133 |
| 60 | 34.255 | 5.925 | 34.058 |
| 61 | 39.234 | 6.394 | 40.452 |
| 62 | 44.938 | 6.797 | 47.250 |
| 63 | 51.471 | 7.025 | 54.275 |
| 64 | 58.953 | 7.006 | 61.281 |
| 65 | 67.523 | 6.710 | 67.991 |
| 66 | 77.339 | 6.162 | 74.153 |
| 67 | 88.583 | 5.381 | 79.534 |
| 68 | 101.400 | 4.506 | 84.040 |
| 69 | 116.210 | 3.675 | 87.715 |
| 70 | 133.103 | 3.114 | 90.829 |
| 71 | 152.453 | 2.657 | 93.487 |
| 72 | 174.616 | 2.185 | 95.672 |
| 73 | 200.000 | 1.701 | 97.372 |
| 74 | 229.075 | 1.252 | 98.624 |
| 75 | 262.376 | 0.884 | 99.509 |
| 76 | 300.518 | 0.491 | 100.000 |
| 77 | 344.206 | 0.000 | 100.000 |

TABLE 1-continued

| No. | Particle diameter (μm) | Frequency (%) | Passing portion cumulative (%) |
|---|---|---|---|
| 78 | 394.244 | 0.000 | 100.000 |
| 79 | 451.556 | 0.000 | 100.000 |
| 80 | 517.200 | 0.000 | 100.000 |
| 81 | 592.387 | 0.000 | 100.000 |
| 82 | 678.504 | 0.000 | 100.000 |
| 83 | 777.141 | 0.000 | 100.000 |
| 84 | 890.116 | 0.000 | 100.000 |
| 85 | 1019.515 | 0.000 | 100.000 |

TABLE 2

| No. | Particle diameter (μm) | Frequency (%) | Passing portion cumulative (%) |
|---|---|---|---|
| 35 | 1.151 | 0.000 | 0.000 |
| 36 | 1.318 | 0.000 | 0.000 |
| 37 | 1.510 | 0.000 | 0.000 |
| 38 | 1.729 | 0.000 | 0.000 |
| 39 | 1.981 | 0.000 | 0.000 |
| 40 | 2.269 | 0.000 | 0.000 |
| 41 | 2.599 | 0.000 | 0.000 |
| 42 | 2.976 | 0.000 | 0.000 |
| 43 | 3.409 | 0.000 | 0.000 |
| 44 | 3.905 | 0.000 | 0.000 |
| 45 | 4.472 | 0.000 | 0.000 |
| 46 | 5.122 | 0.000 | 0.000 |
| 47 | 5.867 | 0.102 | 0.102 |
| 48 | 6.720 | 0.180 | 0.282 |
| 49 | 7.597 | 0.294 | 0.576 |
| 50 | 8.816 | 0.442 | 1.019 |
| 51 | 10.097 | 0.624 | 1.642 |
| 52 | 11.565 | 0.839 | 2.481 |
| 53 | 13.246 | 1.032 | 3.513 |
| 54 | 15.172 | 1.168 | 4.681 |
| 55 | 17.377 | 1.233 | 5.914 |
| 56 | 19.904 | 1.256 | 7.171 |
| 57 | 22.797 | 1.285 | 8.455 |
| 58 | 26.111 | 1.370 | 9.825 |
| 59 | 29.907 | 1.573 | 11.398 |
| 60 | 34.255 | 1.986 | 13.384 |
| 61 | 39.234 | 2.772 | 15.156 |
| 62 | 44.938 | 4.109 | 20.265 |
| 63 | 31.471 | 5.953 | 26.218 |
| 64 | 58.953 | 8.048 | 34.266 |
| 65 | 67.523 | 9.821 | 44.088 |
| 66 | 77.339 | 11.253 | 55.341 |
| 67 | 88.583 | 11.250 | 66.591 |
| 68 | 101.460 | 9.604 | 76.195 |
| 69 | 116.210 | 7.243 | 83.438 |
| 70 | 133.103 | 5.418 | 88.856 |
| 71 | 152.453 | 4.015 | 92.871 |
| 72 | 174.616 | 2.863 | 95.734 |
| 73 | 200.000 | 1.936 | 97.670 |
| 74 | 229.073 | 1.219 | 98.889 |
| 75 | 262.376 | 0.714 | 99.603 |
| 76 | 300.518 | 0.397 | 100.000 |
| 77 | 344.206 | 0.000 | 100.000 |
| 78 | 394.244 | 0.000 | 100.000 |
| 79 | 451.558 | 0.000 | 100.000 |
| 80 | 517.200 | 0.000 | 100.000 |
| 81 | 592.387 | 0.000 | 100.000 |
| 82 | 678.504 | 0.000 | 100.000 |
| 83 | 777.141 | 0.000 | 100.000 |
| 84 | 890.116 | 0.000 | 100.000 |
| 85 | 1019.515 | 0.000 | 100.000 |

TABLE 3

| No. | Particle diameter (μm) | Frequency (%) | Passing portion cumulative (%) |
|---|---|---|---|
| 35 | 1.151 | 0.000 | 0.000 |
| 36 | 1.318 | 0.000 | 0.000 |
| 37 | 1.510 | 0.000 | 0.000 |
| 38 | 1.729 | 0.000 | 0.000 |
| 39 | 1.981 | 0.000 | 0.000 |
| 40 | 2.269 | 0.000 | 0.000 |
| 41 | 2.599 | 0.000 | 0.000 |
| 42 | 2.976 | 0.000 | 0.000 |
| 43 | 3.409 | 0.000 | 0.000 |
| 44 | 3.905 | 0.000 | 0.000 |
| 45 | 4.472 | 0.000 | 0.000 |
| 46 | 5.122 | 0.000 | 0.000 |
| 47 | 5.867 | 0.000 | 0.000 |
| 48 | 6.720 | 0.119 | 0.119 |
| 49 | 7.697 | 0.210 | 0.335 |
| 50 | 8.816 | 0.363 | 0.698 |
| 51 | 10.097 | 0.575 | 1.273 |
| 52 | 11.565 | 0.874 | 2.147 |
| 53 | 13.246 | 1.222 | 3.369 |
| 54 | 15.172 | 1.559 | 4.938 |
| 55 | 17.377 | 1.660 | 6.798 |
| 56 | 19.904 | 2.073 | 8.871 |
| 57 | 22.797 | 2.223 | 11.094 |
| 58 | 20.111 | 2.347 | 13.441 |
| 59 | 29.907 | 2.500 | 15.941 |
| 60 | 34.255 | 2.747 | 18.688 |
| 61 | 39.234 | 3.184 | 21.872 |
| 62 | 44.938 | 3.900 | 25.772 |
| 63 | 51.471 | 4.810 | 30.582 |
| 64 | 58.953 | 5.815 | 36.397 |
| 65 | 67.523 | 6.732 | 43.129 |
| 66 | 77.339 | 7.514 | 50.643 |
| 67 | 88.583 | 7.822 | 58.465 |
| 68 | 101.400 | 7.408 | 65.873 |
| 69 | 116.210 | 6.386 | 72.259 |
| 70 | 133.103 | 5.556 | 77.815 |
| 71 | 152.453 | 4.889 | 82.704 |
| 72 | 174.616 | 4.203 | 86.967 |
| 73 | 200.000 | 3.666 | 90.633 |
| 74 | 229.075 | 3.057 | 93.690 |
| 75 | 262.376 | 2.453 | 96.143 |
| 76 | 300.518 | 1.895 | 98.038 |
| 77 | 344.206 | 1.053 | 99.090 |
| 78 | 394.244 | 0.585 | 99.675 |
| 79 | 451.556 | 0.325 | 100.000 |
| 80 | 517.200 | 0.000 | 100.000 |
| 81 | 592.387 | 0.000 | 100.000 |
| 82 | 678.504 | 0.000 | 100.000 |
| 83 | 777.141 | 0.000 | 100.000 |
| 84 | 890.116 | 0.000 | 100.000 |
| 85 | 1019.515 | 0.000 | 100.000 |

TABLE 4

| Analyte | Average particle diameter | Median diameter | Mode diameter | Ratio of particles having a particle diameter of 30 to 120 μm |
|---|---|---|---|---|
| Example 1 (GAG38) | 61.99 μm | 47.39 μm | 48.19 μm | 53.66% |
| Example 2 (GAG30) | 79.50 μm | 72.51 μm | 72.51 μm | 70.05% |
| Example 3 (GAG22) | 94.79 μm | 76.45 μm | 82.70 μm | 53.40% |

(Results and Remarks)

The results show that particles of the ascorbic acid contained in the ascorbic acid dispersion material of the present invention obtained in Examples 1 to 3 have little deviation in the particle diameter. As a result, usage characteristics upon application onto skin are presumed to be superior.

Test Example 3 X-Ray Diffraction Analysis

The X-ray diffraction analysis of the ascorbic acid crystals contained in the ascorbic acid dispersion material of the present invention obtained in Examples 1 to 3 was carried out. Note that as a control sample, commercially available ascorbic acid was ground using a mortar, and tested alongside.

(Samples for X-Ray Diffraction Analysis)

As a sample for X-ray diffraction analysis, the samples for the scanning electron microscope (particulate powder) manufactured in Test Example 1 were used.

(X-Ray Diffraction Analysis)

The X-ray diffraction analysis of the obtained sample for the X-ray diffraction analysis was carried out using an X-ray diffraction analysis device (device name: XPERT-PRO MPD, produced by PANalytical) under the following conditions.

Conditions:
scanning range: (° 2θ): 10.000 to 30.00
target: Cu
X-ray output setting: 40 mA, 45 kV
step size (° 2θ): 0.017
type of scanning: continuous
sample width (mm): 10.00

Figure 9:
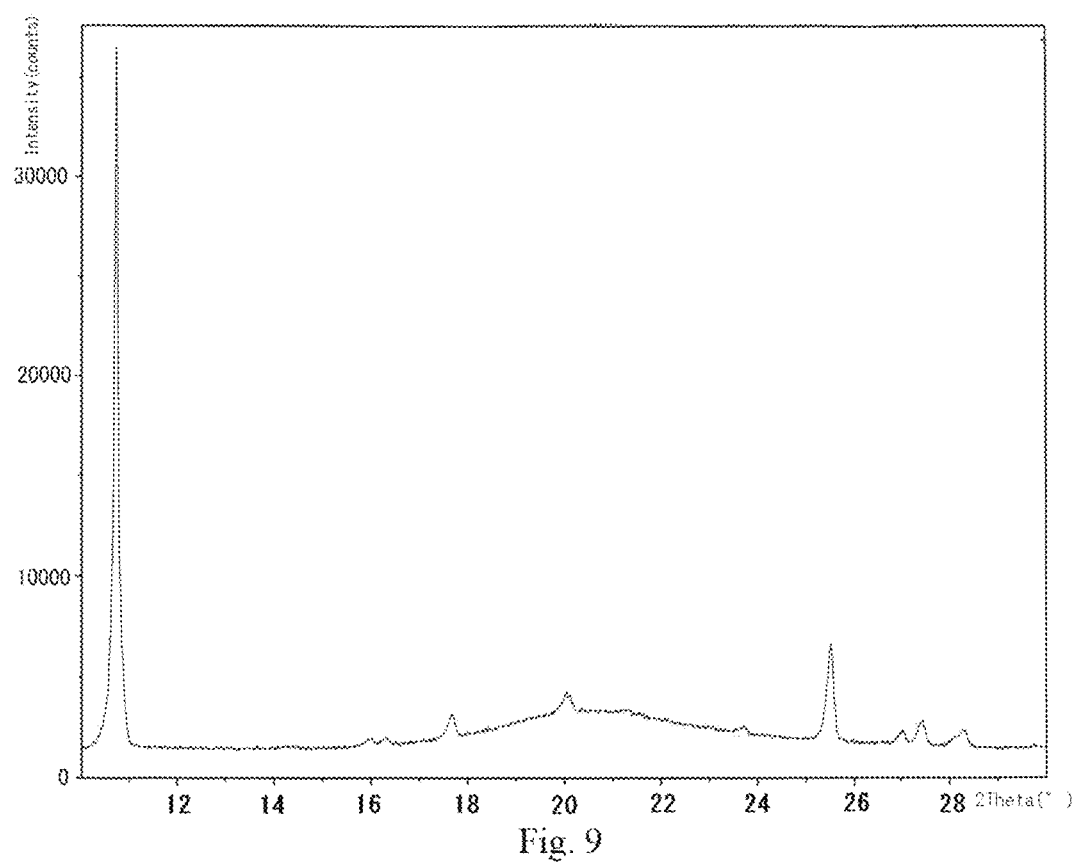
FIG. 9 is a chart illustrating the results of the X-ray diffraction analysis of the ascorbic acid crystal in Example 2.
Figure 10:
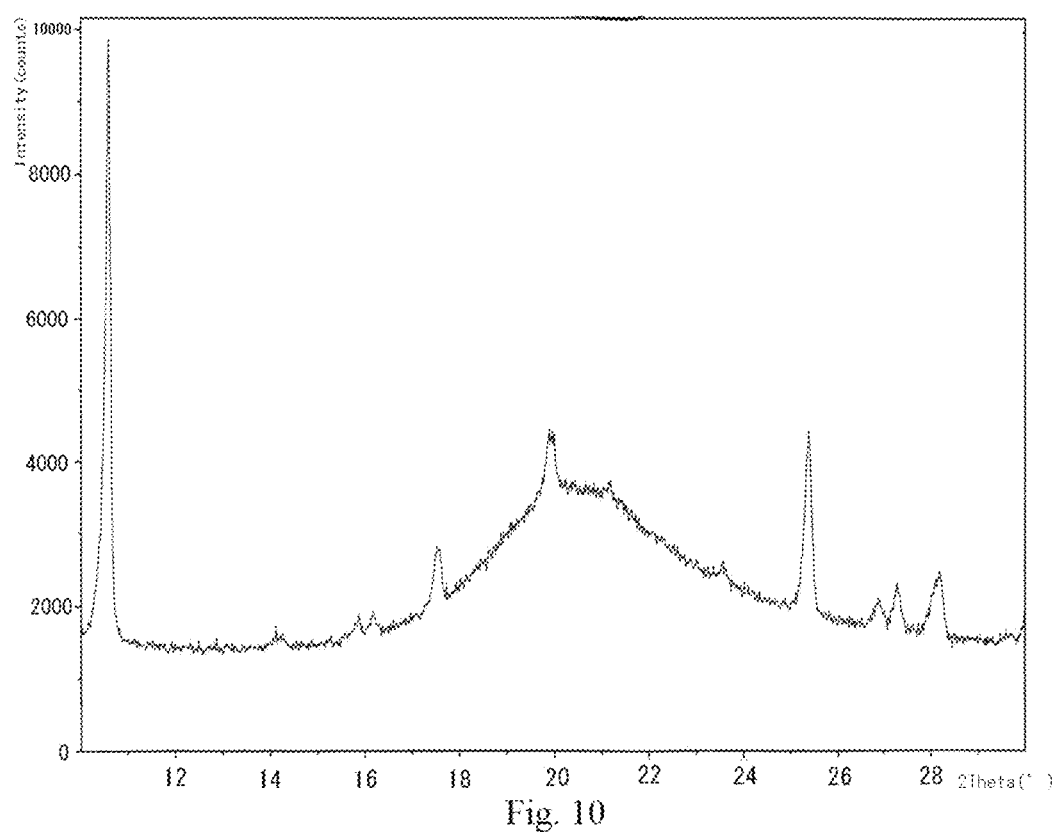
FIG. 10 is a chart illustrating the results of the X-ray diffraction analysis of the ascorbic acid crystal in Example 3.

The obtained results are shown in FIG. 9 (Example 1: GAG38), FIG. 10 (Example 2: GAG30), and FIG. 11 (Example 3: GAG22).

(Results and Remarks)

The results show that in the X-ray diffraction analysis, the ascorbic acid crystals contained in the ascorbic acid dispersion material of the present invention obtained in Examples 1 to 3 includes peaks of 2θ angles at 10.6, 15.9, 16.2, 17.6, 20.0, 25.4, 27.0, 27.3 and 28.2 degrees (±0.2 degrees). As a result, these crystals have a specific crystal structure.

Test Example 4 Viscosity Analysis

A viscosity analysis of the ascorbic acid dispersion material of the present invention obtained in Examples 1 to 3 was carried out.

The viscosity analysis regarding the ascorbic acid dispersion material of the present invention obtained in Examples 1 to 2 was carried out using a Brookfield viscometer (trade name: RVDV-I+, manufactured by BROOKFIELD) under the following conditions.

Conditions:
temperature: 20 degrees
rotation speed: 6 r/min, after 1 minute
rotor No: No. 7

The ascorbic acid dispersion material of the present invention obtained in Example 3 was measured using a Brookfield viscometer (trade name: LVDV-I+, produced by BROOKFIELD) under the following conditions.

Conditions:
temperature: 20 degrees
rotation speed: 6 r/min, after 1 minute
rotor No: No. 64

The obtained results are shown in Table 5.

TABLE 5

| Analyte | Test results |
| --- | --- |
| Example 1 (GAG38) | 210000 mPa · s |
| Example 2 (GAG30) | 130000 mPa · s |
| Example 3 (GAG22) | 9700 mPa · s |

(Results and Remarks)

The obtained results show that the ascorbic acid dispersion material of the present invention has a higher viscosity as the ascorbic acid concentration increases.

The results also show that the viscosity of the ascorbic acid dispersion material of the present invention obtained in Examples 1 to 3 is a suitable viscosity as an application agent onto skin, etc. As a result, usage characteristics upon application onto skin are presumed to be superior.

Test Example 5 Density Analysis

A density analysis of the ascorbic acid dispersion material of the present invention obtained in Examples 1 to 3 was carried out.

Density was measured using a dry automatic densimeter (trade name: AccuPycII, produced by Shimadzu Corporation).

The results thereof are shown in Table 6.

TABLE 6

| Analyte | Average density |
| --- | --- |
| Example 1 (GAG38) | 1.3876 g/cm$^3$ |
| Example 2 (GAG30) | 1.3548 g/cm$^3$ |
| Example 3 (GAG22) | 1.3260 g/cm$^3$ |

(Results and Remarks)

The results show that the ascorbic acid dispersion material of the present invention has a higher density as the ascorbic acid concentration increases, and it is an appropriate density.

Moreover, the ascorbic acid dispersion material of the present invention obtained in Examples 1 to 3 has superior usage characteristics upon application onto skin, and has properties of the density obtained by this testing, in addition to the abovementioned properties.

The above results show that the ascorbic acid dispersion material of the present invention has higher chemical stability, and has superior usage characteristics, such as spreadability and smoothness, upon application onto skin.

What is claimed is:

1. A manufacturing method of an ascorbic acid dispersion material, comprising:
    a heating step of adding an ascorbic acid into a solvent consisting of one or more selected from the group consisting of glycerin, diglycerin, polyglycerin represented by a following formula (1), and propylene glycol, and heating a mixture of the ascorbic acid and the solvent to a temperature of 100 to 125° C. to dissolve the ascorbic acid in the solvent;
    a cooling step of cooling the mixture with the ascorbic acid dissolved therein at a cooling rate of 5 to 20° C./min until a temperature of the solution reaches 35 to 50° C. to remove heat from the solution; and
    a growth step of storing the solution after completion of the cooling step at 27 to 38° C. for a period of 5 hours or longer to promote crystal growth so that the ascorbic acid crystal has a flat plate shape, a thickness of 0.05 to 3 μm, and an average particle diameter of 50 to 100 μm,
    wherein n is an integer from 3 to 10,

[Chemical formula 1]

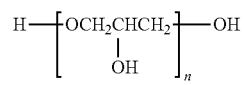

wherein a particle size distribution of the ascorbic acid crystal has a distribution such that a particle diameter of 30 to 120 μm is 40 to 80% of overall particles.

2. The manufacturing method of ascorbic acid dispersion material according to claim 1, wherein the ascorbic acid concentration is 20 to 40 wt %.

3. The manufacturing method of ascorbic acid dispersion material according to claim 1, wherein an average density in an ascorbic acid dispersion material is 1.3 to 1.4 g/cm$^3$.

4. The manufacturing method of ascorbic acid dispersion material according to claim 1, wherein the viscosity in an ascorbic acid dispersion material is 5000 to 300,000 mPa·s.

5. The manufacturing method of ascorbic acid dispersion material according to claim 1, wherein a particle size distribution of the ascorbic acid crystal has a distribution such that a particle diameter of 1.151 to 29.907 μm is 11.398-28.133%, a particle diameter of greater than 29.907 to 133.103 μm is 61.874-77.458%, and a particle diameter of greater than 133.103 μm is 9.171-22.185%, with respect to the overall particles in a total of 100%.

\* \* \* \* \*